(12) United States Patent
Swan (10) Patent No.: US 6,206,694 B1
(45) Date of Patent: Mar. 27, 2001

(54) HANDPIECE ASSEMBLY FOR AIR ABRASION

(75) Inventor: Jawn P. Swan, Los Angeles, CA (US)

(73) Assignee: Crystalmark Dental Systems, Inc., Glendale, CA (US)

( * ) Notice: Subject to any disclaimer, the term of this patent is extended or adjusted under 35 U.S.C. 154(b) by 0 days.

(21) Appl. No.: 09/449,139

(22) Filed: Nov. 24, 1999

(51) Int. Cl.[7] ............................. A61C 3/02; A61G 15/00
(52) U.S. Cl. ........................ 433/88; 433/79; 206/369; 206/379
(58) Field of Search ................... 206/369, 63.5, 206/379; 433/80, 88, 77, 79

(56) References Cited

U.S. PATENT DOCUMENTS

| | | |
|---|---|---|
| 2,641,839 | 6/1953 | Black . |
| 4,386,611 | 6/1983 | Kantorski et al. . |
| 4,820,152 | 4/1989 | Warrin et al. . |
| 5,192,206 | 3/1993 | Davis et al. . |
| 5,312,250 | * 5/1994 | Ellman et al. ................. 433/77 |
| 5,368,161 | * 11/1994 | Plais ............................. 206/369 |
| 5,967,779 | 10/1999 | Brassil et al. . |
| 6,113,867 | * 9/2000 | Mayer ........................... 422/300 |

OTHER PUBLICATIONS

Website: http://cranews.com/newsletter/highlights/97–12/abrasive/ideal.htm Dec. 1997.

* cited by examiner

Primary Examiner—Nicholas D. Lucchesi
(74) Attorney, Agent, or Firm—Sheldon & Mak (57) ABSTRACT

The invention is directed towards a handpiece assembly for use with air abrasion apparatuses used in a wide spectrum of applications and industries. This handpiece assembly comprises the following components: (1) a handle comprising a proximal end and a distal end; the distal end also comprising an attachment means for attaching the handle of the handpiece assembly to the air abrasion apparatus; (2) a quick-releasing and quick-connecting socket comprising a male portion and a female portion; and (3) a nozzle comprising a proximal end and a distal end; the distal end of the nozzle provides the male portion of the socket and the proximal end of the handle provides the female portion of the socket. The distal end of the nozzle also fits into the proximal end of the handle to form the quick-releasing and quick connecting socket. This novel handpiece assembly may further comprise an articulating socket located towards the proximal end of the nozzle. These features of the invention provide a handpiece where the nozzle can be quickly released or disconnected from, and reconnected to, the handle, thus providing facile exchange of nozzles of varying shapes and sizes, as needed to accomplish the a desired task. The invention also includes a kit for dental use comprising the handpiece, a dental mirror and a sterilizable tray for holding instruments.

20 Claims, 5 Drawing Sheets

HANDPIECE ASSEMBLY FOR AIR ABRASION

BACKGROUND

Air abrasion technology is used in a variety of applications where there is a need to cut, drill, clean, or to add texture to various substrates. When a substrate is fragile, however, only a gentle process, such as air abrasion, can be considered.

The technique of air abrasion utilizes fine abrasives, such as aluminum oxide, silicon carbide, bicarbonate of soda, crushed nut shells, glass beads and ground plastics, which are introduced into a compressed gas stream, such as air, and directed through a nozzle to the surface to be abraded.

Currently, air abrasion technology is used in a wide range of industries, such as in the manufacture of semiconductor devices and electronic components, as well as in the aerospace and automotive industries. Air abrasion is also used by artists for engraving in glass or other brittle, fragile materials. Museums utilize air abrasion in art and artifact restoration. Paleontologists use air abrasion for uncovering fossils. Air abrasion technology is also used in the medical treatment field. For example, dermatologists use air abrasion to abrade the skin so as to encourage new skin growth. Dentists also use air abrasion for cleaning and texturing teeth, and for cavity detection and preparation.

In applying the technique of air abrasion, a nozzle assembly, usually attached to a handpiece, is required for directing the air and abrasive stream to the surface to be abraded.

The prior art describes a handpiece for use in air abrasion in which the nozzle can be unscrewed from the handle portion to permit changing the nozzle head during an application. However, during certain applications, such as in dentistry, the act of changing nozzles by the steps of unscrewing, disassembling, rescrewing and reassembling is very cumbersome and inconvenient. In fact, the difficulty of changing nozzle heads during an application actually may impede the use of the appropriately shaped and/or sized nozzle for the particular task at hand.

In the art of air abrasion, as it is applied to dental care, an ideal air abrasion unit was described as having eighteen ideal characteristics. An ideal characteristic that was found to be absent in the air abrasion art was an air abrasion handpiece with a nozzle that is capable of disconnecting quickly. See www.cranews.com/newsletter/highlights/97-12/abrasive/ideal. Another desirable feature for an air abrasion unit used in dental care is that the handpiece should be sterilizable and constructed to withstand certain sterilization procedures, such as autoclaving. Id.

Thus, there is a recognized need in the art of air abrasion for a handpiece equipped with nozzles that are capable of quickly disconnecting and reconnecting to the handle portion of an air abrasion device during an application. Moreover, for certain applications involving air abrasion, it is desirable that a handpiece be able to withstand sterilization procedures. If these needs could be met, the user of air abrasion equipment would be better able to accomplish a particular task involving air abrasion.

SUMMARY

The present invention is directed to a handpiece assembly that satisfies the need in the art of air abrasion for a quick-releasing and quick5 connecting device for changing nozzles during an application. The inventive handpiece assembly is also completely sterilizable. Moreover, the handpiece assembly of the present invention can be used with air abrasion apparatuses in a variety of industrial and health environments either for manual or automated use.

The handpiece assembly includes a handle with a proximal end and a distal end. The distal end of the handpiece assembly includes a means for attaching the handle of the handpiece assembly to an air abrasion apparatus. The handpiece assembly also includes a quick-releasing and quick-connecting socket or joint, which contains a male portion and a female portion, and forms the joint for connecting the handle to the nozzle. The nozzle includes a proximal end, comprising a tip portion and a distal end, which comprises a male plug which provides the male portion of the socket. The proximal end of the handle provides the female portion of the socket. The distal end of the nozzle fits into the proximal end of the handle to form the quick-releasing and quick connecting socket or joint.

This handpiece assembly can also include an articulating or rotating socket or joint, located towards the distal end of the nozzle. The nozzle portion of the handpiece assembly further comprises a tip suitably sized and shaped for a particular task involving air abrasion. The distal end of the tip portion of the nozzle fits into the proximal end of the male plug to form the articulating or rotating socket or joint.

The handpiece assembly can be constructed of any material suitable to direct the abrasive stream produced generally by the jetting of a fine powder and gas. Preferably the handpiece is largely constructed from a corrosion resistant material, such as stainless steel, ceramics and plastics. Stainless steel is particularly suited for applications where sterilization of the handpiece is required, such as for applications in dental care.

Another aspect of the present invention involves a method of using the handpiece assembly with an air abrasion apparatus. The steps of this novel method include first attaching the handpiece to a hose attached to an air abrasion apparatus, followed by changing the quick-releasing and quick-connecting nozzle for another quick-releasing and quick-connecting nozzle with an appropriately shaped tip to better accomplish the desired task, and then directing the tip portion of the nozzle to a surface in need of abrasion.

Still another aspect of the invention is an autoclavable kit for use with air abrasion dental equipment. The kit includes an autoclavable tray to organize, and hold in place, the handpiece assembly of the present invention during sterilization and use. The kit also includes a dental mirror and handle.

DRAWINGS

These and other features, aspects and advantages of the present invention will become better understood with reference to the following description, appended claims, and accompanying drawings where:

DESCRIPTION

The present invention satisfies the long felt need in the art of air abrasion for an air abrasion handpiece with a quick-change nozzle/tip assembly. The present invention satisfies this need by incorporating a quick-releasing and quick-connecting socket or joint, in a handpiece assembly as the connecting device between a handle and a nozzle, as well as providing a handpiece that can withstand sterilization without degradation.

The following definitions apply to the novel handpiece of the present invention:

"Air abrasion" or "air abrasion jetting" is defined as any technique where a mixed stream of an abrasive substance and a gas, or where fluid-laden abrasive steams, are provided in an air abrasion apparatus for cutting, drilling, texturing, cleaning and/or removal of surface particles and/or debris.

A "handpiece assembly" means any handpiece comprising at least a handle and a nozzle.

A "handle" means any tubular handling device used for attachment to an air abrasion apparatus at one end and for attachment to a nozzle at the other end; a handle, in accordance with the present invention, can be handheld or attached to an automated device.

An "attachment means" for connecting a handle portion of the handpiece assembly can be any means that can suitably attach a handle portion of a handpiece to a tubing of an air abrasion apparatus and also permit free flow of an abrasive mixture. This attachment means includes, but is not limited to, a screw thread with or without an o-ring, a quick-releasing and quick-connecting socket with or without an articulating joint or a luer fitting, a luer lock or a luer valve.

A "nozzle" means any tubular device that is shaped for its intended application and that also provides the final conduit of an abrasive mixture to the intended surface for application of an air abrasion apparatus.

A "quick-releasing and quick-connecting socket" means any socket that is capable of quickly disconnecting or releasing the connectivity between a handle and a nozzle of a handpiece assembly, and/or any socket that is capable of quickly connecting to form the connectivity between a handle and a nozzle of a handpiece assembly.

An "articulating socket" means any socket or joint that is capable of rotation, thereby providing a point of articulation.

The present invention is directed to a handpiece assembly designed to be used with any air abrasion apparatus or abrasive jet machining device. Currently these devices are used in a wide variety of applications spanning the aerospace, semiconductor, automotive, medical device and equipment, and electronic industries, and in dental offices for intra-oral use.

The handpiece assembly of the present invention comprises a handle portion shaped to comfortably fit a user's hand or shaped to fit with an automated device, and a nozzle portion, which includes an appropriately shaped and sized tip suitable to the task of directing an abrasive stream to a particular surface requiring abrasion. The tip may be either tubular, block shaped, or any other shape and/or size, including orifice size, that is suitable for a desired task.

A need for quickly changing the nozzle portion of the handpiece assembly exists for many reasons. Among these reasons is the need to replace worn nozzles and to vary the size and shape of the tip so as to better accomplish the task at hand.

One example of an application for the handpiece assembly of the present invention is in dental care. A dentist while using an air abrasion device may want to use several different nozzles during a procedure. The invention allows the dentist to quickly change the nozzle portion so as to vary the shape and/or size of the tip to suit the application. A feature of the novel handpiece of the present invention that is of particular importance in the field of dentistry is the ability of this handling device to be sterilized without degradation.

Another feature of present invention is an articulating or rotatable joint. In a preferred embodiment this articulating joint is located towards the distal end of the tip portion of the nozzle. This feature provides an air abrasion handpiece assembly with a discharge nozzle that can be readily adjusted to any angle by means of a ball joint.

Figure 1:
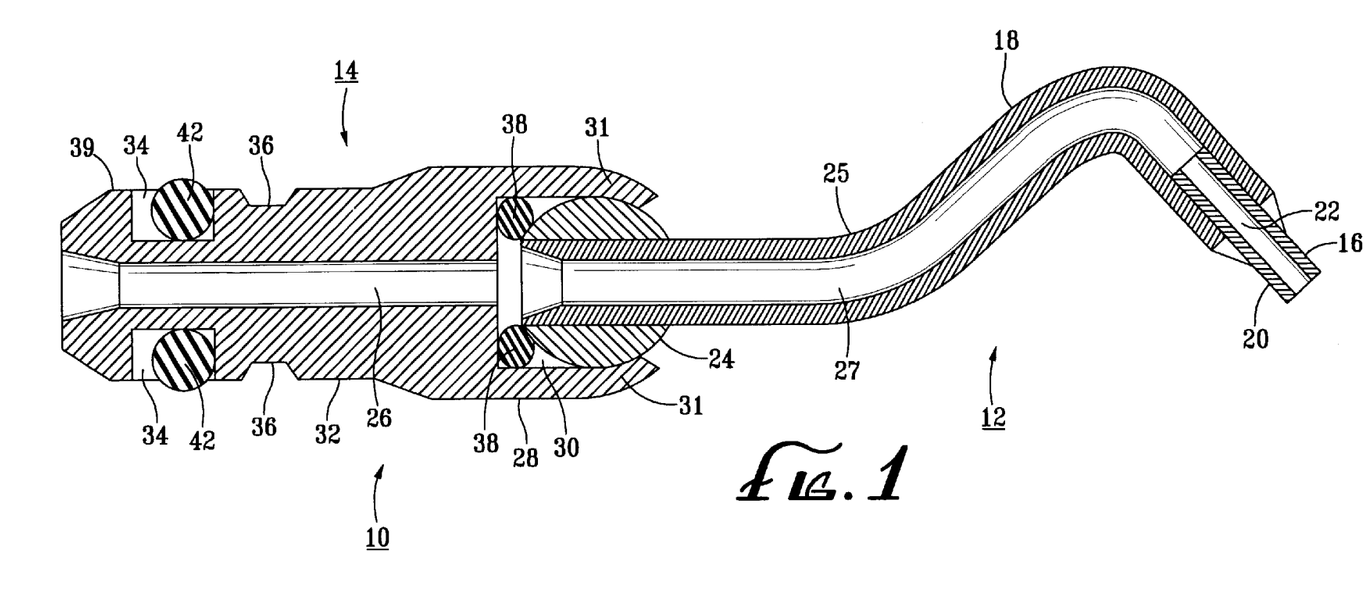
FIG. 1 is a longitudinal/cross-sectional view of the nozzle portion of a handpiece assembly of the present invention.

In a preferred embodiment, the handpiece assembly comprises a nozzle 10, shown in FIG. 1, which includes a tip portion 12 comprising the proximal end of the nozzle, and a male plug 14 comprising the distal end of the nozzle. The handpiece assembly is preferably composed of stainless steel components, however, other materials, such as ceramic or powdered metals also are suitable for use in the present invention. The nozzle is assembled by inserting a 0.20" long carbide tube 16 into a stainless steel tube 18. Other suitable materials that can be used in lieu of carbide are sapphire, ceramic and powdered metals. In this embodiment, the carbide tube 16 has an outer diameter of 0.052" 20 and an inner diameter 22 ranging from 0.005" to 0.032". At the distal end of the tip portion, a stainless steel ball 24 is placed. This ball also may be made of ceramics or powdered metals in lieu of stainless steel. In this preferred embodiment, both the carbide tube 16 and the stainless steel ball 24 are attached by using silver solder, which is capable of withstanding high temperatures during sterilization. Other materials for attaching either the tube or the ball are various high temperature epoxys. In this embodiment, the stainless steel tube 18 of the tip portion is approximately 1.5" long with an outer diameter of 0.096" 25 and an inner diameter of 0.55" 27. The stainless steel ball 24 has a diameter of approximately 0.187". Following assembly of the tip portion, the tip can be bent into a variety of shapes as desired.

Figure 2:
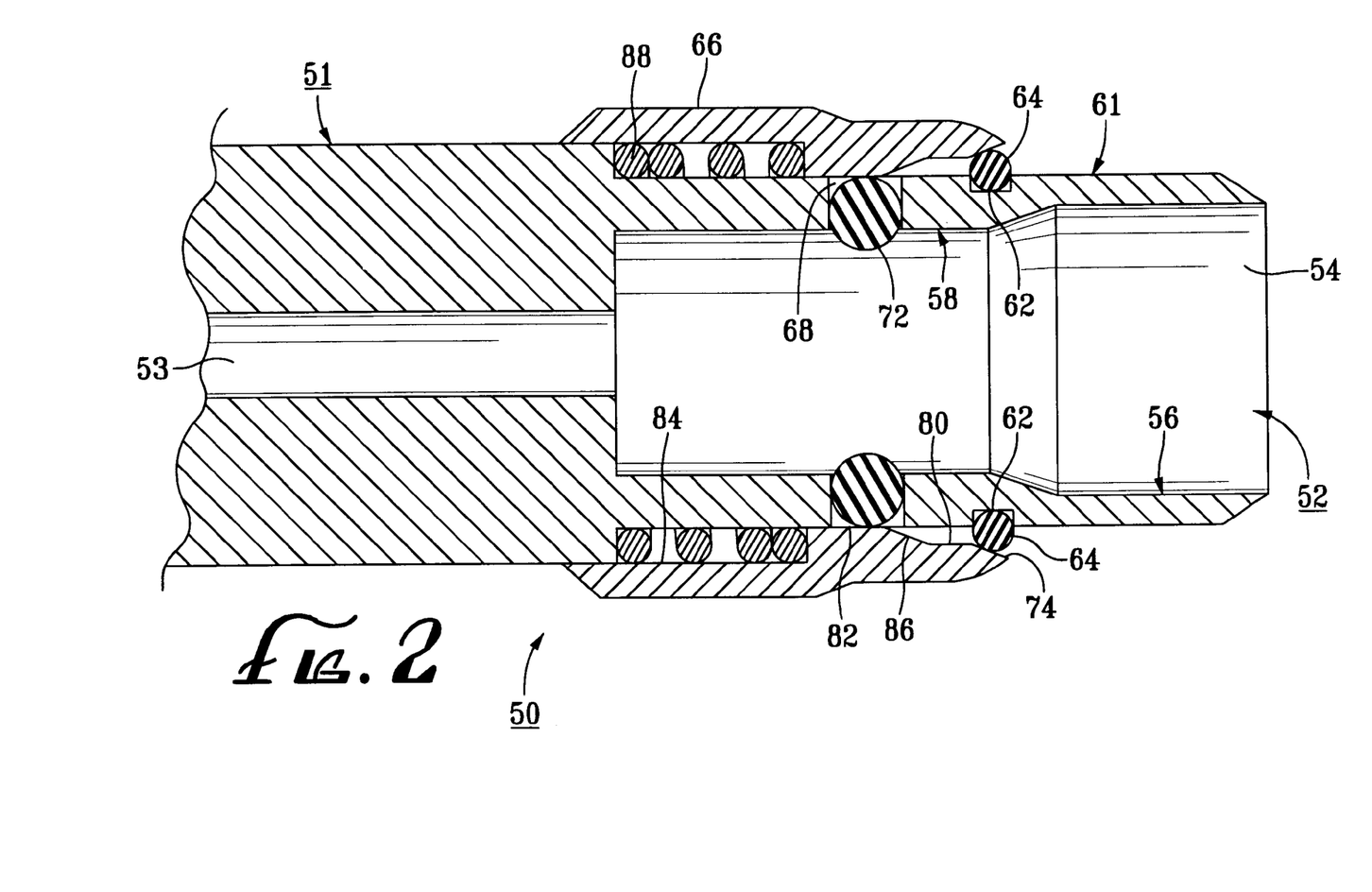
FIG. 2 is a longitudinal/cross-sectional view of the handle portion of a handpiece assembly in the locked position shown without the male plug of the nozzle.
Figures 3A, 3B:
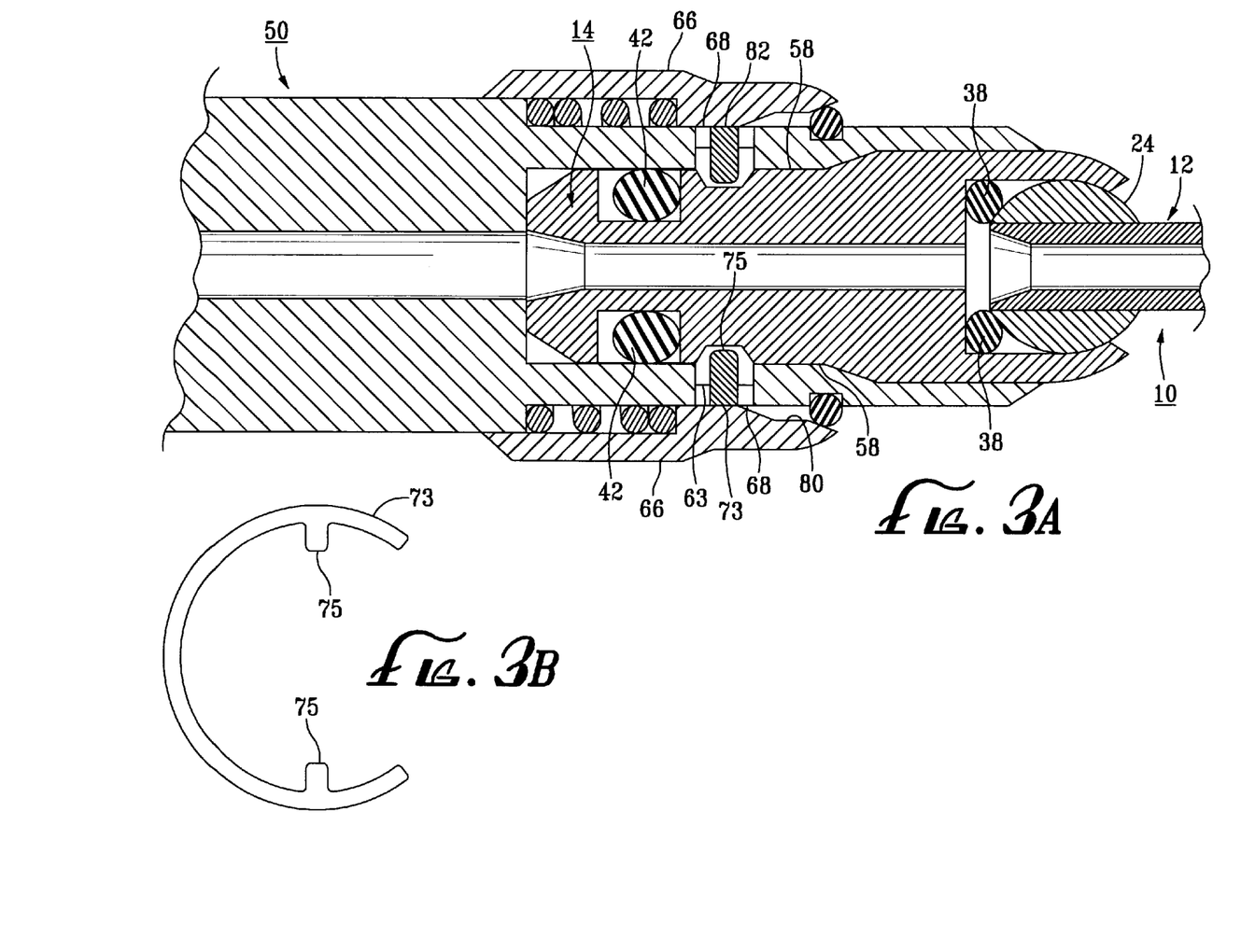
FIG. 3a is a longitudinal/cross-sectional view of the handle portion of the handpiece assembly of the present invention, shown with the male plug of the nozzle inserted into the female portion of the handle; in this figure, an alternative locking mechanism, utilizing a locking spring clip is depicted.
FIG. 3b shows the locking spring clip apart from the handle.

The male plug 14 comprising the distal end of the nozzle is also preferably comprised of stainless steel, ceramics or powdered metals. The male plug has a longitudinal hole 26 in the center so as to direct the flow of an abrasive mixture to the end of the tip. The male plug is tapered towards its distal end with a larger diameter 28 located at the proximal end of the plug. The larger diameter 28 of the male plug 14 comprises a counter bore 30 for accepting the steel ball. The counter bore 30 is made in such a manner to create thin walls 31 to facilitate the swagging of the tip portion into place in the nozzle assembly. The second outside diameter 32 of the male plug portion has an o-ring groove 34 near the distal end of the male plug 14. A locking groove 36 is located between the o-ring groove 34 and the large diameter 28 for a locking ball 72 or a locking spring clip 73 to drop into, thereby providing a locking mechanism between the nozzle 10 and the handle 50, as shown in FIG. 2 or FIG. 3. Diameter 39 on the distal end of the nozzle is slightly larger than the second outside diameter 32 thereby creating a failsafe in the possible event that the locking ball or locking spring clip mechanism wear.

A compliant, heat resistant material, such as a silicone o-ring 38, is placed into the counter bore 30 end of the male plug 14 into which the ball end of the tip assembly is inserted. The ball 24 is placed against the o-ring 38 and is capable of being rotated due to the thin wall of the counter bore 30. Thus, in rotating the joint, there is constant pressure on the o-ring 38. This assembly of the tip portion 12 to the male plug 14 forms a leak-proof ball joint with an angle of motion approximately 40 degrees in any direction that does not impede the flow of an abrasive mixture. A silicone o-ring 42 is placed into the o-ring groove 34 of the male plug/tip assembly. This o-ring 42 provides a seal between the nozzle 10 assembly and the handle 50 when these components of the handpiece assembly are connected.

A preferred embodiment of the handle portion 50 of the handpiece assembly is shown in FIG. 2. The air abrasion handpiece assembly of the present invention, in addition to the nozzle described above, comprises a main body 51 which forms the handle portion 50 of the assembly. The handle 50 further comprises the female component 52 of the quick-releasing and quick-connecting socket of the present invention. In the preferred embodiment, the handle 50 is shaped to fit comfortably in the hand of a user, or shaped to accommodate an automated use of the inventive handpiece.

At the distal end there is a means for attachment (not shown) of the handle portion 50 of the hand-piece assembly to a hose of an air abrasion apparatus. The attachment means located at the distal end of the handle can comprise a second quick-releasing and quick-connecting mechanism, similar to the mechanism described herein for attaching the handle to the nozzle. This attachment means can also comprise screw threads with or without an o-ring seal, or a luer fitting, luer lock or a luer valve. In the embodiment shown in FIG. 2, the main body 51 of the handle 50 is largely comprised of stainless steel. However, the main body 51 may be composed of other materials, such as ceramics or plastics. The handle 50 further comprises a longitudinal hole 53 to accommodate the compressed gas and abrasive mixture On the proximal end of the handle is a counter bored hole 54 into which the male plug of the nozzle assembly fits. The bored hole 54 has two diameters. The first diameter 56, towards the proximal end of the handle, is larger than the second diameter 58 which is distal to the first diameter 56. The transition from the first diameter 56 to the second diameter 58 is gradual to facilitate the o-ring seal 42 located on the male plug 14. The larger diameter 56 supports the ball end 24 of the male plug 14 of the nozzle when the handle and the nozzle are connected. On the same end the outside diameter 61 is turned down to reduce the overall size of the handle. This reduction in diameter provides a stop for the compression spring 88 and creates a smooth transition from outside diameter of the main body 51 to a locking collar 66. One or more holes 68 are cross drilled from the outside turned down diameter 61 to the smaller inside diameter 58. A groove 62 accepts a retaining snap ring 64 for holding the locking collar 66 onto the handpiece assembly.

As shown in FIG. 2, the locking collar 66 has four inside diameters. The first diameter is a pocket 74 for the snap ring 64 that holds the locking collar 66 onto the handpiece assembly. The pocket 74 also serves to prevent any of the part of the novel handpiece to scratch or irritate the surface to be abraded, especially during patient care. The second inside diameter 80 creates a space for entry of the locking ball 72 or balls 72 when the locking collar 66 is pulled back to either remove or insert the male plug 14 of the nozzle assembly 10. The third diameter 82 is the smallest and is connected to the second diameter 80 at a slope. This slope connecting the diameters creates a cam 86. When the cam 86 is forward, that is, pushed by the compression spring 88, the locking collar 66 moves into the locked position. The steel ball(s) 72 are then pushed into the inside diameter 58 of the handpiece assembly until the third diameter 82 of the locking collar 66 is in contact with the steel balls, thus causing the ball(s) to protrude into the inside diameter 58 of the handpiece assembly. When the locking collar 66 is pulled back the ball(s) 72 can now be displaced into the second diameter 80, which allows removal or insertion of the male plug 14 of the nozzle assembly 10. The fourth diameter 84 is on the opposite end of the snap ring 64 pocket 74. This diameter allows for the compression spring 88. The compression spring 88 then forces the locking collar 66 to push the ball(s) 72 into the locking position.

Alternatively, as shown in FIG. 3a and FIG. 3b, a groove 63 may be utilized in the locking device located on the handle portion 50 of the handpiece assembly. This groove is designed to accept a locking spring clip 73 with lobe(s) 75 that protrude through the hole(s) 68 and into and past the diameter 58, thus providing an alternative mechanism for locking the handpiece assembly. FIG. 3a further illustrates the male plug 14 locked onto the handle 50 of the handpiece assembly of the present invention. FIG. 3a also depicts certain features of the male plug 14 and the tip portions 12, such as the ball joint 24 placed against an o-ring 38, and the o-ring seal 42.

As an alternative to the locking mechanism shown in FIG. 2, the locking spring clip 73 with lobe(s) 75, instead of the steel ball(s) 72, is pushed into the inside diameter 58 of the handpiece assembly until the third diameter 82 of the locking collar 66 is in contact with the outside of the locking spring clip 73, thus causing the inside lobe(s) 75 to protrude into the inside diameter 58 of the handpiece assembly. When the locking collar 66 is pulled back the lobe(s) 75 can now be displaced into the second diameter 80, with the removal or insertion of the male plug 14 of the nozzle assembly 10.

Another aspect of the present invention arises mainly with the use of air abrasion technology as it is applied in the field of dentistry. Dentists must incorporate infection control procedures and processes into their practice. Currently, air abrasion is a modality that is used in many dental practices. As such, portions of air abrasion equipment must be capable of sterilization. In this regard, the handpiece assembly of the present invention is completely sterilizable.

To accomplish the task of sterilization of air abrasion dental equipment, the present invention includes an air abrasion autoclavable kit. This kit includes a tray that provides a compact system to conveniently arrange and hold the items used in an air abrasion procedure, such as the components of the handpiece assembly, i.e., the handle and an assortment of nozzles, and a dental mirror assembly, including a detachable mirror/handle assembly, such as the dental mirror assembly disclosed in U.S. Ser. No. 09/219, 555 and incorporated herein by reference. The autoclavable tray, along with these basic hand tools used in air abrasion, are designed to be placed into an autoclave or to be used with other types of sterilization methods.

After sterilization, the air abrasion kit also can be used in the treatment process. The detachable handpiece of the present invention, including a variety of differently shaped nozzles with varying diameters, or orifices, and the handle portion, a dental mirror and mirror handle, are all easily accessible and organized for use in the autoclavable tray of the present invention. Following the air abrasion procedure, the items are then cleaned, detached and put back in place on the autoclavable tray, ready for re-sterilization.

Figure 4:
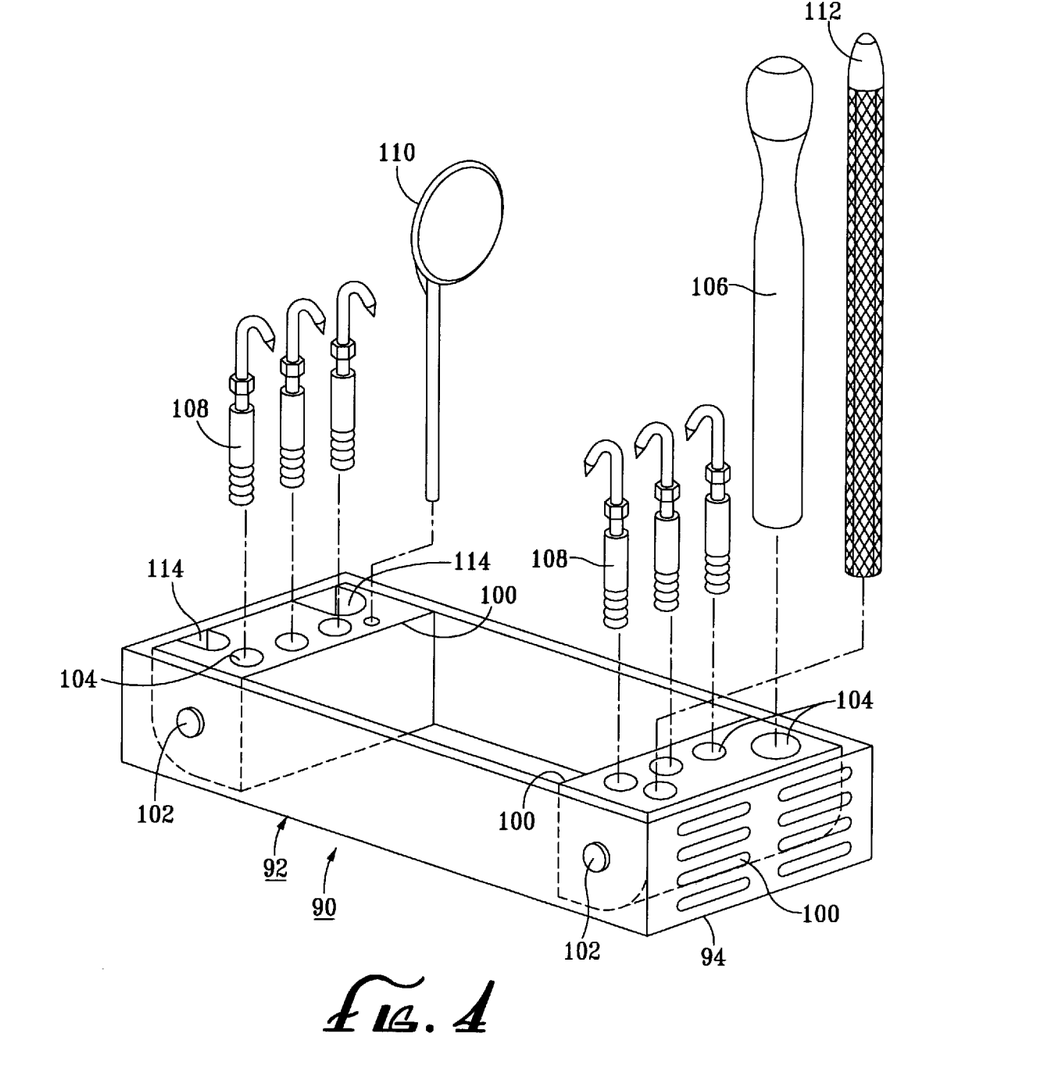
FIG. 4 illustrates a sterilizable tray of the present invention comprising the handpiece of the present invention and other air abrasion dental hand tools, in position for insertion into the tray.
Figure 5:
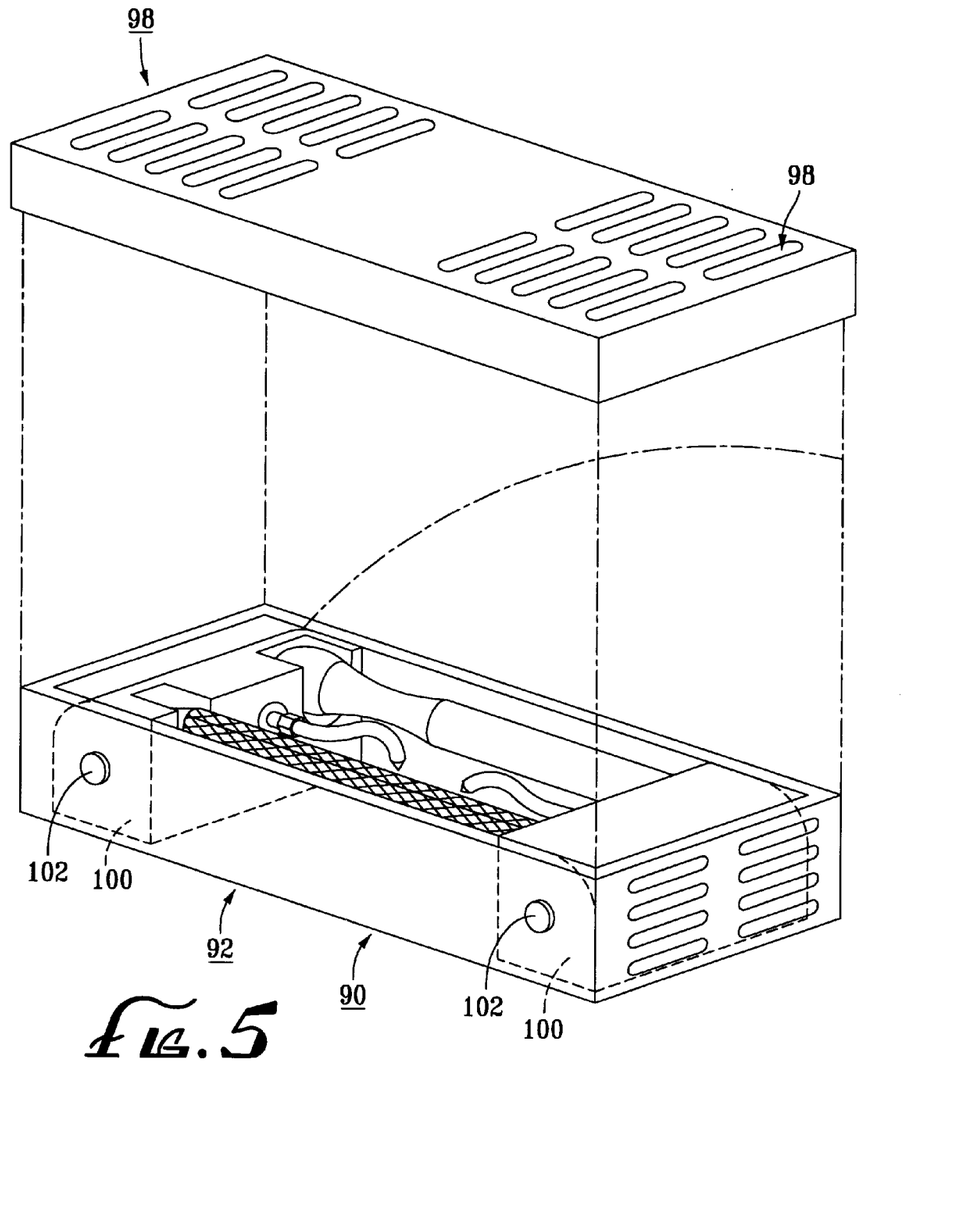
FIG. 5 illustrates a sterilizable tray comprising air abrasion dental tools shown in their sterilization/storage position.

The autoclavable tray of the present invention 90, suitable for use with the handpiece described herein, is illustrated in FIG. 4 and in FIG. 5. In FIG. 4, the tray consists of a bottom portion 92 made from metal, plastic or any suitable material that can tolerate the heat and chemicals used to sterilize medical/dental instruments. The bottom portion 92 has vent holes 94 along the ends of the bottom portion. The lid 96, shown in Figure 5, also has vent holes 98. These vent holes 94 and 98 allow the sterilization medium to circulate, as well as provide for rapid evaporation of the medium upon drying. The bottom portion 92 comprises end blocks 100 that rotate in on a pivot 102 located at or near the center of the block ends 100. The blocks 100 have suitably sized and shaped holes 104 for holding the handle 106 of the handpiece assembly, a variety of differently sized or shaped nozzles 108, a mirror 110 and mirror handle 112. In FIG. 5, the blocks 100 are shown in the upright position being loaded with the dental instruments.

In FIG. 5, these end blocks 100 are depicted following rotation around the pivots 102 so as to fold the dental hand equipment inward in a secure manner for use during the sterilization process and subsequent handling. A lid portion 114, also containing vent holes 98, is depicted prior to encasing the dental hand tools in the tray. Further, as shown in FIG. 4 pockets 112 in one block allow the longer handle of the handpiece assembly 106 and mirror handle 112 to nest in a compact and secure manner.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112.

What is claimed is:

1. A handpiece assembly for use with an air abrasion apparatus comprising:
   a handle comprising a proximal end and a distal end, wherein the distal end comprises an attachment means for attaching the handle of the handpiece assembly to the air abrasion apparatus;
   a quick-releasing and quick-connecting socket comprising a male plug portion, comprising a proximal end and a distal end, and a female portion;
   a nozzle comprising a proximal end, which comprises a tip portion, comprising a proximal end and a distal end, wherein the distal end of the nozzle provides the male plug of the socket and the proximal end of the handle provides the female portion of the socket, and wherein the distal end of the nozzle fits into the proximal end of the handle to form the quick-releasing and quick connecting socket.

2. The handpiece assembly of claim 1, further comprising an articulating socket located towards the distal end of the tip portion of the nozzle.

3. The handpiece assembly of claim 2, wherein the distal end of the tip portion fits into a hole, located at the proximal end of the male plug, to form the articulating socket.

4. The handpiece assembly of claim 2, wherein the articulating socket comprises a counter bore and a ball.

5. The handpiece assembly of claim 4, wherein the counter bore and the ball provide a joint capable of spherical rotation about an axis coincidental with the longitudinal tubular opening running through the nozzle and/or the longitudinal tubular opening running through the handle.

6. The handpiece of claim 4, wherein an o-ring is placed near the end of the counter bore forming the ball joint seal at or near the rotation point of the socket.

7. The handpiece assembly of claim 1, wherein the handle further comprises a locking collar located on the female portion of the quick-releasing and quick-connecting socket for locking the handle to the nozzle of the handpiece assembly.

8. The handpiece assembly of claim 7, wherein the locking collar comprises a locking ball or locking spring clip.

9. The handpiece assembly of claim 1, wherein a longitudinal tubular opening runs through the handle to the nozzle to the tip portion of the nozzle for passage of an abrasive mixture.

10. The handpiece assembly of claim 1, wherein the attachment means comprises either a female portion or a male portion of a second quick-releasing and quick-connecting socket.

11. The handpiece assembly of claim 10, wherein the second quick releasing and quick connecting socket comprises an articulating joint capable of rotation.

12. The handpiece assembly of claim 1, wherein the attachment means is connected to a hose and wherein the hose is connected to the air abrasion apparatus.

13. The handpiece assembly of claim 12, wherein handpiece and the hose are sterilizable.

14. The handpiece assembly of claim 1, wherein the attachment means comprises screw threads, a luer fitting, a luer lock or luer valve.

15. A method of using the handpiece assembly of claim 1 with an air abrasion apparatus comprising:
   attaching the handpiece assembly to a hose, wherein the hose is attached to an air abrasion apparatus;
   changing the quick-releasing and quick-connecting-socket for another quick-releasing and quick-connecting socket with an appropriately shaped tip to accomplish a task involving air abrasion; and
   directing the tip portion of the nozzle to a surface in need of abrasion.

16. The method of claim 15, wherein the task is abrading teeth for the purpose of providing dental care.

17. The handpiece assembly of claim 1, wherein the handpiece is used with an automated air abrasion apparatus.

18. A kit for use with air abrasion dental equipment comprising:
   the handpiece assembly of claim 1;
   a dental mirror assembly comprising a mirror portion and a handle portion; and
   a tray comprising suitably sized compartments for organizing and holding the components of the handpiece assembly and the mirror assembly during sterilization and/or during use.

19. An sterilizable device for holding dental hand tools used in air abrasion comprising:
- a tray comprising at least a bottom portion and a lid portion and composed of suitable material to withstand a sterilization procedure, wherein the bottom portion and the lid portion of the tray comprise holes for ventilation;
- at least two end blocks comprising a top portion, side portions, a bottom portion and a pivot, wherein the pivot is located near or at the center of the block ends, and wherein the block ends are capable of at least rotation inwards, towards the center of the tray, with a rotation angle of approximately 90 degrees;
- at least two differently shaped compartments located on the top portion of the end blocks which are suitably shaped to hold the dental hand tools, wherein upon inward rotation about the pivot, the compartments are facing inward towards the center of the tray so as to allow the hand tools to lie across the bottom of the tray.

20. The tray of claim 19, wherein the compartments are suitably shaped for holding a dental handpiece assembly, comprising at least a nozzle and a handle, a dental mirror assembly, comprising at least a mirror portion and a handle, and at least one other compartment for holding additional nozzles and/or additional mirrors.

* * * * *